United States Patent [19]

Alty et al.

[11] Patent Number: 5,466,850
[45] Date of Patent: Nov. 14, 1995

[54] PROCESS FOR THE PREPARATION OF FLUOROSILANES

[75] Inventors: Adam C. Alty, Gainesville; Simon F. Sellers, Hawthorne, both of Fla.

[73] Assignee: PCR, Inc., Gainesville, Fla.

[21] Appl. No.: 418,272

[22] Filed: Apr. 7, 1995

[51] Int. Cl.⁶ ................................................ C07F 7/08
[52] U.S. Cl. .................................................... 556/477
[58] Field of Search .................................... 556/477

[56] References Cited

U.S. PATENT DOCUMENTS

| | | | |
|---|---|---|---|
| 2,527,233 | 10/1950 | Sowa | 556/477 |
| 2,713,063 | 7/1955 | Sommer | 556/477 |
| 2,927,938 | 3/1960 | Cohen et al. | 556/477 |
| 3,621,045 | 11/1971 | Muller et al. | 556/477 |
| 3,646,092 | 2/1972 | Dathe | 556/477 |
| 3,655,714 | 4/1972 | Dathe | 556/477 |

FOREIGN PATENT DOCUMENTS 92305192  6/1992  European Pat. Off. .

OTHER PUBLICATIONS

Homma, J. Electro. Chem. Soc., 140, 2046 (1993).
Homma, J. Electro. Chem. Soc., 140, 687 (1993).
Booth, J. Amer. Chem. Soc., 68, 2655 (1946).
Marans, J. Amer. Chem. Soc., 73, 5127 (1951).
Peppard, J. Amer. Chem. Soc., 68, 76 (1946).

*Primary Examiner*—Paul F. Shaver
*Attorney, Agent, or Firm*—Hedman, Gibson & Costigan

[57] ABSTRACT

The invention is directed to the preparation of fluorosilanes, such as, for example, alkyl, cycloalkyl, aryl, alkoxy, aryloxy and siloxy fluorosilanes by the action of hydrogen fluoride on substrates containing at least one silicon-hydride bond.

13 Claims, No Drawings

PROCESS FOR THE PREPARATION OF FLUOROSILANES

FIELD OF THE INVENTION

This invention relates to fluorosilanes which are especially useful as substrates used in the chemical vapor deposition (CVD) of silicon-oxy-fluoride films on surfaces. More particularly, the present invention relates to a process for the preparation of fluorosilanes by the reaction of hydrogen fluoride on materials containing silicon hydride bonds.

BACKGROUND OF THE INVENTION

The utility of fluorosilanes, especially alkoxyfluorosilanes, as agents of CVD is widely known. For example, fluorotriethoxysilane is useful in the electronics industry for the fabrication of semiconductor devices. The fluorotriethoxysilane may be used to deposit fluoride containing silicon oxide film using a variety of techniques including plasma deposition, e.g., Homma EP 92-305 192; Spin-on-glass Homma, J. Electro. Chem. Soc., 140, 2046 (1993) and catalytic CVD Homma, J. Electro. Chem. Soc., 140, 687 (1993). The films deposited have excellent step coverage and are useful as interlayer dielectric films.

A variety of synthetic methods for the preparation of fluorosilanes are known to those skilled in the art. One general method known is the conversion of other silicon halides, in particular silicon chlorides to silicon fluorides by the action of halogen exchange fluorination agents. This can be achieved using a variety of reagents such as metal fluorides and hydrogen fluoride. Specific examples in the literature include Booth, J. Amer. Chem. Soc., 68, 2655 (1946) in which butyltrichlorosilane is converted to butyltrifluorosilane in low yield by the action of antimony trifluoride; furthermore, Marans, J. Amer. Chem. Soc., 73, 5127 (1951) demonstrates the halogen exchange converting triethylchlorosilane to triethylfluorosilane in 81% yield using 48% aqueous hydrofluoric acid.

Another general method is the substitution of a fluoride for an alkoxy or aryloxy group bonded to silicon. Examples of this approach include Marans (as above) wherein, for example, di-n-propyldiethoxysilane is converted to di-n-propyldifluorosilane in 52% yield by reaction with 48% aqueous hydrofluoric acid. Tetraethoxysilane may be converted to fluorotriethoxysilane as described by Peppard, J. Amer. Chem. Soc., 68, 76, 1946 by the reaction of antimony trifluoride catalyzed by antimony pentachloride; or, as described by Homma (as above) by the reaction of hydrogen fluoride.

The existing technologies suffer generally from low yields, the use of excess amounts of fluorinating agents or expensive reagents, and the generation of reactive by-products such as hydrogen chloride or ethanol. Thus, there continues to exist the need for a process which gives high yields of silicon fluorides from commercially available and inexpensive starting materials.

SUMMARY OF THE INVENTION

According to the present invention, silicon hydride substrates, such as, for example, alkyl, cycloalkyl, alkoxy, aryl, aryloxy or siloxy silanes containing at least one silicon hydride bond, are treated with hydrogen fluoride to give high yields of the corresponding silicon fluorides with the concomitant generation of hydrogen. In one embodiment of the invention hydrogen fluoride is contacted with triethoxysilane to give a near quantitative yield of fluorotriethoxysilane, with surprisingly little contamination of the desired product by material formed by substitution of fluoride for ethoxy.

The present invention contemplates therefore a process for producing fluorosilanes, the process comprising
 (a) reacting
  (i) a substrate compound having one or more silicon hydride bonds selectively with
  (ii) hydrogen fluoride, alone, or in admixture with an inert gas, under hydrogen eliminating conditions until the reaction is substantially complete; and
 (b) recovering
  (i) a reacted substrate compound having one or more silicon fluoride bonds,
  (ii) a mixture of such reacted substrate compounds or
  (iii) an oligomeric derivative of (i) or (ii).

In its preferred features, the invention provides such a process in which the substrate compound is of the formula

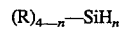

$$(R)_{4-n}\text{—SiH}_n$$

wherein R is an organic group and n is an integer of from 1 to 3, and, particularly, a process in which the substrate compound is of the formula

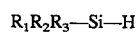

$$R_1R_2R_3\text{—Si—H}$$

wherein $R_1$, $R_2$, and $R_3$, independently, are selected from alkyl, cycloalkyl, aryl, alkoxy, aryloxy, siloxy or hydrogen, or a mixture of any of the foregoing; a process in which hydrogen fluoride is contacted with a silicon hydride containing substrate at temperatures within a range from about −40° C. to about +200° C. and at pressures from within a range of about full vacuum to about 200 psig; especially one in which the reaction temperature is from about +10° C. to about +100° C.

Preferred embodiments of the invention embrace such processes in which the hydrogen generated is either removed from the reaction mass physically or chemically, or is contained within the reaction; those wherein the reactants are contacted either in a batch operation or in a continuous reactor; those which are carried out with a reaction mixture consisting essentially of the silicon hydride substrate (a)(i) and hydrogen fluoride, alone, or in admixture with an inert gas (a)(ii); those carried out with a reaction mixture comprising the silicon hydride substrate (a)(i), hydrogen fluoride, alone or in admixture with an inert gas (a)(ii), and an inert liquid medium (a)(iii), at a temperature of between about the freezing point of the medium to about the boiling point of the medium.

Special mention is made of a process as defined above which comprises contacting hydrogen fluoride with triethoxysilane with the introduction of said hydrogen fluoride either in the gas or liquid phase to generate as the principal product fluorotriethoxysilane; as defined above which comprises contacting triethylsilane with hydrogen fluoride to generate triethylfluorosilane and hydrogen; a process which comprises contacting a silicon hydride containing substrate and hydrogen fluoride in the presence of the product mixture from the reaction of a tetraalkoxysilane or alkylalkoxysilane such that the conversion to a fluorosilane is enhanced; and a process which comprises contacting triethoxysilane with pyridinium poly(hydrogen fluoride) to generate fluorotriethoxysilane.

DETAILED DESCRIPTION OF THE INVENTION

We have found surprisingly that silanes of the general formula $R_1R_2R_3SiH$ where $R_1$, $R_2$ and $R_3$ can be alkyl, cycloalkyl, aryl, alkoxy, aryloxy, siloxy or hydrogen can be treated with hydrogen fluoride to produce the corresponding fluorosilane $R_4R_5R_6SiF$ where $R_4$, $R_5$, $R_6$ are alkyl, cycloalkyl, aryl, alkoxy, aryloxy, siloxy or fluoride in high yield with little or no by-product formation other than the generation of hydrogen.

$R_1$, $R_2$ and $R_3$ may comprise hydrocarbyl groups where $R_1$ and/or $R_2$ and/or $R_3$ are aliphatic or cycloaliphatic alkyl wherein $R_n$ is $C_1$–$C_{30}$; $R_1$ and/or $R_2$ and/or $R_3$ is alkoxy or alkyl alkoxy with $R_n$ $C_1$–$C_{10}$; $R_1$ and/or $R_2$ and/or $R_3$ may also be aryl or aralkyl or aryloxy or aralkyloxy with $R_n$ $C_6$–$C_{30}$ or siloxy. The substrates may also contain more than one silicon hydride bond, so $R_1$ and/or $R_2$ and/or $R_3$ may represent hydrogen radicals. The substrates may be partially fluorinated so $R_1$ and/or $R_2$ and/or $R_3$ may represent fluoride radicals.

Specific examples of silanes useful as hydrogen fluoride reactive substrates in accordance with the present invention include, but are not limited to, trimethylsilane, triethylsilane, tripropylsilane, methyldiethylsilane, triphenylsilane, phenyldimethylsilane, dimethylsilane, diethylsilane, diphenylsilane, methylphenylsilane, trimethoxysilane, triethoxysilane, methyldimethoxysilane, phenyldimethoxysilane, phenoxysilane, dimethylphenoxysilane, 6-chlorohexyldimethylsilane, 4-chlorobenzyldimethylsilane, tris (methoxyethoxy)silane, pentamethyldisiloxane, 1,1,2,2-tetramethyldisiloxane, tris(trimethylsiloxy)silane, and the like, mixtures of any of them and the like, alone, and in admixture with dimers, trimers, and other oligomers thereof.

The selectivity of the reaction forming the basis of the invention is particularly surprising in the case where $R_1$ and/or $R_2$ and/or $R_3$ is alkoxy or aryloxy. In these cases it would be expected for hydrogen fluoride to react with the alkoxy or aryloxy groups to generate the fluorosilane and corresponding alcohol. However, we have found that the silicon hydride bond reacts preferentially with hydrogen fluoride under mild reaction conditions with the generation of relatively few fluoride for alkoxy substituted products. In fact, it is one preferred embodiment of this invention to improve, for example, the reaction of tetraethoxysilane with hydrogen fluoride by the subsequent addition of triethoxysilane to remove unreacted hydrogen fluoride from the system enhancing process yields and ease of purification.

The hydrogen fluoride utilized in the reaction may be substantially anhydrous or be added as an aqueous solution. The hydrogen fluoride is, however, preferably anhydrous. The hydrogen fluoride may be contacted with the silane in the gas or liquid phase. The hydrogen fluoride may also be introduced as a salt, for example an amine salt, or as a stabilized liquid such as pyridinium poly(hydrogen fluoride).

A feature of the reaction, in all cases, is the generation of hydrogen which may preferably be removed continuously from the reaction. The reactions can be run successfully at subatmospheric or superatmospheric pressure, however, the reactions are generally run at atmospheric pressure.

The reaction is generally conducted at ambient to moderate temperatures, although reduced temperatures down to −40° C. or temperatures of up to 200° may be utilized, depending upon the physical properties and reactivity of the substrate.

Solvents useful in this invention are inert solvents that do not degrade under the reaction conditions. Solvents such as toluene, xylene or heptane may be used. The reaction is most preferably carried out in the absence of solvent in the cases where the substrate to be treated with hydrogen fluoride is a liquid.

Preferably the reaction contents are agitated to maintain a well mixed solution and the hydrogen fluoride is fed into the reaction to maintain control of the heat generated. External cooling may be applied to the reaction vessel. The process may be run either in a batch manner or in a continuous manner, such as the concurrent feed of the substrate and hydrogen fluoride through a static mixer. The products can be isolated using conventional purification techniques such as distillation.

DESCRIPTION OF THE PREFERRED EMBODIMENTS

The following examples illustrate the present invention, but the claims are not to be construed as limited thereto.

EXAMPLE 1

A 1-gallon stirred stainless steel reactor was loaded with 2550 g of triethoxysilane. Gaseous anhydrous hydrogen fluoride, 311 g, was then added subsurface during a period of 1½ hours. The temperature was controlled to less than 25° C. by recirculation of ice water through internal cooling coils. After stirring for 16 hours at room temperature analysis by Gas Chromatography (GC) showed the composition to be 2.2% ethanol, 2.9% fluorodiethoxysilane, 3.6% difluorodiethoxysilane, 8.6% triethoxysilane, 80.2% fluorotriethoxysilane and 1.6% tetraethoxysilane. After heating to 40°–50° C. for about 80 hours the composition was 0.6% difluorodiethoxysilane, 0.25% triethoxysilane, 89.1% fluorotriethoxysilane and 10.1% tetraethoxysilane.

EXAMPLE 2

The same reactor was charged with 800 g of tetraethoxysilane. Gaseous anhydrous hydrogen fluoride, 77 g, was then added in an equivalent manner to example 1. After stirring for 16 hours at 50° C. analysis by GC showed the composition to be 26.6% ethanol, 10.7% difluorodiethoxysilane, 40.7% fluorotriethoxysilane, 14.5% tetraethoxysilane and 7.39% siloxane oligomers. Triethoxysilane, 600 g was then added portionwise over a period of two hours. After heating to 50° C. analysis by GC showed the composition to be 0.17% fluorodiethoxysilane, 0.22% difluorodiethoyxsilane, 3.8% triethoxysilane, 43.7% fluorotriethoxysilane, 44.5% tetraethoxysilane and 7.64% siloxane oligomers.

EXAMPLE 3

The same reactor was charged with 500 g of triethylsilane. Gaseous anhydrous hydrogen fluoride, 86 g, was then added in an equivalent manner. After stirring at 50° C. for 18 hours analysis by GC showed the composition to be 42.1% triethylsilane and 56.2% fluorotriethylsilane (97% yield based upon 100% conversion of the starting material).

EXAMPLE 4

The same reactor was charged with 300 g of diethylsilane. Gaseous anhydrous hydrogen fluoride, 50 g, was then added in an equivalent manner. A GC showed the composition to be 62.8% diethylsilane, 21.0% fluorodiethylsilane and 8.6% difluorodiethylsilane.

EXAMPLE 5

A 500 ml Teflon flask was charged with 10 g of triethoxysilane. Aqueous hydrofluoric acid (50%), 1 ml, was added very slowly to control the exotherm to less than 60° C.

Analysis by GC showed the composition to be 32.4% ethanol, 4.0% fluorodiethoxysilane, 43.2% triethoxysilane and 9.2% fluorotriethoxysilane.

The patents, patent applications and publications cited above are incorporated herein by reference.

While there have been described what are presently believed to be preferred embodiments of the invention, it will be apparent to a person skilled in the art that numerous changes can be made in the ingredients, conditions and proportions set forth in the foregoing embodiments. For example, the silicon hydride can be dissolved in a solvent, such as toluene, xylene or heptane and treated with gaseous hydrogen fluoride, an amine salt of hydrogen fluoride, or a stablized liquid form of hydrogen fluoride, such as pyridinium poly(hydrogen fluoride). The reaction can be carried out continuously in a loop reactor comprising cooling zones for controlling the heat of reaction. All such obvious modifications can be employed without departing from the invention as described herein and as defined in the appended claims.

What we claim is:

1. A process for producing fluorosilanes, said process comprising
   (a) reacting
      (i) a substrate compound having one or more silicon hydride bonds selectively with
      (ii) hydrogen fluoride, alone, or in admixture with an inert gas, under hydrogen eliminating conditions until the reaction is substantially complete; and
   (b) recovering
      (i) a reacted substrate compound having one or more silicon fluoride bonds,
      (ii) a mixture of such reacted substrate compounds or
      (iii) an oligomeric derivative of (i) or (ii).

2. A process as defined in claim 1 wherein said substrate compound is of the formula $(R)_{4-n}$—$SiH_n$ wherein R is an organic group and n is an integer of from 1 to 3.

3. A process as defined in claim 2 wherein said substrate compound is of the formula $R_1R_2R_3$—Si—H wherein $R_1$, $R_2$, and $R_3$, independently, are selected from alkyl, cycloalkyl, aryl, alkoxy, aryloxy, siloxy or hydrogen, or a mixture of any of the foregoing.

4. A process as defined in claim 1 wherein hydrogen fluoride is contacted with a silicon hydride containing substrate at temperatures within a range from about −40° C. to about +200° C. and at pressures from within a range of about full vacuum to about 200 psig.

5. A process as defined in claim 4 wherein the reaction temperature is from about +10° C. to about +100° C.

6. A process as defined in claim 4, wherein the hydrogen generated is either removed from the reaction mass physically or chemically, or is contained within the reaction.

7. A process as defined in claim 4 wherein the reactants are contacted either in a batch operation or in a continuous reactor.

8. A process as defined in claim 1 carried out with a reaction mixture consisting essentially of the silicon hydride substrate (a)(i) and hydrogen fluoride, alone, or in admixture with an inert gas (a)(ii).

9. A process as defined in claim 1 carried out with a reaction mixture comprising the silicon hydride substrate (a)(i), hydrogen fluoride, alone or in admixture with an inert gas (a)(ii), and an inert liquid medium (a)(iii), at a temperature of between about the freezing point of the medium to about the boiling point of the medium.

10. A process as defined in claim 1 which comprises contacting hydrogen fluoride with triethoxysilane with the introduction of said hydrogen fluoride either in the gas or liquid phase to generate as the principal product fluorotriethoxysilane.

11. A process as defined in claim 1 which comprises contacting triethylsilane with hydrogen fluoride to generate triethylfluorosilane and hydrogen.

12. A process as defined in claim 1 which comprises contacting a silicon hydride containing substrate and hydrogen fluoride in the presence of the product mixture from the reaction of a tetraalkoxysilane or alkylalkoxysilane such that the conversion to a fluorosilane is enhanced.

13. A process as defined in claim 1 which comprises contacting triethoxysilane with pyridinium poly(hydrogen fluoride) to generate fluorotriethoxysilane.

* * * * *